United States Patent [19]

Gurfinkel et al.

[11] Patent Number: 5,231,180
[45] Date of Patent: Jul. 27, 1993

[54] PROCESS FOR THE MANUFACTURE OF DIAZINON

[75] Inventors: Elkana Gurfinkel, Omer; Yaakov Shmueli, Beer-Sheva, both of Israel

[73] Assignee: Makhteshim Chemical Works, Ltd., Beer-Sheva, Israel

[21] Appl. No.: 851,458

[22] Filed: Mar. 16, 1992

Related U.S. Application Data

[63] Continuation-in-part of Ser. No. 482,585, Feb. 21, 1990, abandoned.

[30] Foreign Application Priority Data

Sep. 28, 1989 [IL] Israel .................................. 91824

[51] Int. Cl.⁵ .......................................... C07F 9/6512
[52] U.S. Cl. ..................................... 544/243; 544/319
[58] Field of Search ............................................ 544/243

[56] References Cited

U.S. PATENT DOCUMENTS

| | | | |
|---|---|---|---|
| 2,754,243 | 7/1956 | Gysin et al. | 544/243 |
| 4,323,678 | 4/1982 | Schilling | 544/243 |
| 4,654,329 | 3/1987 | Reifschneider | 514/86 |
| 4,898,942 | 2/1990 | Ovadia et al. | 544/243 |
| 5,034,529 | 7/1991 | Freeman | 544/243 |

*Primary Examiner*—Mukund J. Shah
*Assistant Examiner*—Matthew V. Grumbling
*Attorney, Agent, or Firm*—Browdy and Neimark

[57] ABSTRACT

Diazinon is prepared by converting the starting hydroxypyrimidine to its potassium salt by reacting it with potassium carbonate in an organic solvent after removal of the water by azeotropic distillation, and reacting the resulting non-aqueous salt with diethyl thiophosphoryl chloride and recovering the diazinon formed. The solvent used is either MIBK or an aliphatic hydrocarbon desirably containing 1–20% MEK.

36 Claims, No Drawings

PROCESS FOR THE MANUFACTURE OF DIAZINON

This is a continuation-in-part of parent co-pending application Ser. No. 07/482,585, filed Feb. 21, 1990, now abandoned the contents of which are hereby incorporated by reference.

FIELD OF THE INVENTION

The present invention concerns an improved process for preparing diazinon which, owing to its good insecticidal and acaricidal properties, is of great commercial value for the destruction of insect pests.

BACKGROUND OF THE INVENTION

Diazinon was produced for the first time by Glysin and Margot by reacting 2-isopropyl-4-methyl-6-hydroxy-pyrimidine (hereafter hydroxypyrimidine) with diethylthiophosphoryl chloride (hereinafter TPC) in an inert solvent, in the presence of potassium carbonate as described in United Kingdom patent number 713,278.

In this heterogeneous reaction the potassium pyrimidin-olate is initially formed by heating the hydroxypyrimidine with potassium carbonate in benzene, with simultaneous removal of the water formed. The potassium salt so produced is then reacted with TPC by heating for several hours, the potassium chloride formed extracted by washing with water, and the solvent removed under reduced pressure.

The standard process for the industrial manufacture of diazinon is carried out essentially by means of a 4-stage synthesis, as follows:

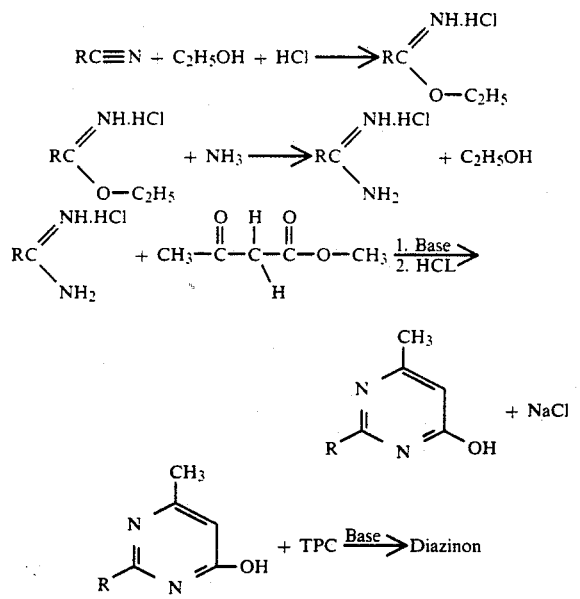

where R is isopropyl.

Since 1952 numerous patents have issued which have attempted to improve upon the above four-step process. Thus, U.S. Pat. No. 4,111,976 describes an improved optimized formation of the product of the first step.

U.S. Pat. No. 4,014,879 describes an optimum continuous ring closure reaction between the amidine and methyl acetoacetate of the third step.

U.S. Pat. Nos. 4,018,771; 4,052,396 and 4,052,397 describe processes of preparing the hydroxy pyrimidine starting with diketene, where the process of the first two patents respectively are run in the presence of a Lewis acid.

United Kingdom patent 2,083,814 describes a process for preparing the hydroxypyrimidine by reacting the iminoether of the first step with ammonia in methanol as solvent and then reacting the resulting amidine of the second step with excess alkyl acetoacetate in methanol under strongly alkaline conditions.

U.S. Pat. No. 3,205,231 describes a process of preparing 2-fluoromethyl derivatives of the hydroxy-pyrimidine by reacting the 2-fluoromethyl hydroxypyrimidine with an organophosphorous ester halide in the presence of dry, sifted potassium carbonate and lower aliphatic ketones or nitrites as solvent.

U.S. Pat. No. 3,792,132 describes a process for preparing alkyl phenyl phosphates and phosphorothionates, where the phenolic compound is reacted with the organophosphorous compound in the presence of a catalyst system comprising a tertiary amine and an alkali or alkaline earth metal in a ketone or carboxylic acid esters as solvent.

Since 1952 several processes have been described in the literature, which modify the fourth (last) step. Thus, U.S. Pat. No. 4,066,642 describes simultaneously reacting TPC and the hydroxypyrimidine in the presence of an acid acceptor such as sodium or potassium hydroxide while refluxing the inert solvent to remove the water as it is formed without the use of any catalyst.

Various other processes involving the use of a variety of catalysts to shorten the reaction times have been described. Suitable catalysts disclosed are mercury salts (U.S. Pat. No. 3,107,245), copper chloride (U.S. Pat. No. 3,107,246), copper nitrate (U. S. Pat. NO. 3,367,935) and basic copper oxide (Japanese patent specification 75 5249 58).

U.S. Pat. No. 4,326,059 describes a process for preparing diazinon, where the hydroxypyrimidine is reacted with aqueous sodium hydroxide in an aromatic hydrocarbon such as xylene, in the presence of a phase transfer catalyst, by first distilling off the water and then adding the TPC. However, this process requires a reaction time of 4 to 6 hours and still yields strongly colored material.

In the processes which involve the use of catalysts it was found that significant amounts of highly toxic by-products such as thiotepp (mono- or di-thiono-tetra-ethyl pyrophosphate) are formed. The presence of even small amounts of these by-products in diazinon is undesirable from the point of view of operators or warm blooded animals that may come into contact therewith. Thus, U.S. Pat. No. 3,432,503 discloses a method of removing these by-products by refluxing the diazinon in an inert solvent in the presence of a base such as sodium hydroxide. However, this process not only requires a separate step subsequent to manufacture, but also involves considerable loss of product during work-up.

Recently U.S. Pat. No. 4,323,678 reported a one-pot reaction wherein isobutyryl-aminocrotonic acid amide is cyclized in the presence of an alcohol, the resulting sodium pyrimidinolate precipitated by addition of a non-polar solvent, the alcohol/water removed by fractionation and the sodium pyrimidinolate reacted with TPC at a temperature of 100° C. to 130° C.

More recently, U.S. Pat. No. 5,034,529 reported a process involving mixing MIBK with the hydroxypyrimidine and sodium hydroxide solution, heating the mixture to reflux and azeotropically distilling off water and then adding TPC. While this process works in a reasonable fashion on a laboratory scale, the azeotropic distillation has been found to take too much time (14–20 hours) when carried out industrially.

All of the above methods suffer from a variety of drawbacks. Examples are long reaction times, the need to use catalysts, the need for tricky manipulation of solvents, and/or the need for a separate step to remove toxic by-products. And none of these processes affords high yields of very pure, very slightly colored diazinon.

SUMMARY OF THE INVENTION

It is an object of the invention to overcome deficiencies in the prior art, such as indicated above.

It is another object of the present invention to provide an improved method for preparing diazinon.

It is a further object of the present invention to provide a method more economical than known methods for the production of diazinon substantially free of toxic by-products in high yields and very high purity, being only very slightly colored.

It has unexpectedly been discovered that diazinon can be prepared by an improved method which comprises reacting wet or dry hydroxypyrimidine with thiophosphorylchloride (TPC) wherein an organic solvent, either methyl-isobutyl ketone (MIBK), aliphatic hydrocarbons or a mixture of both, most desirably petroleum ether having a boiling point of about 60°–140° C., cyclohexane, octane and heptane, is mixed with the hydroxypyrimidine and the water is azeotropically distilled off; dry solid potassium carbonate is added, and when the first mentioned solvent is a hydrocarbon, methyl-ethylketone (MEK) is optionally added; less than a stoichometric amount of TPC is then added to react with the hydroxypyrimidine and form the desired diazinon; and the resultant diazinon is then recovered.

By means of the present process commercially satisfactory reaction rates are achieved with yields of some 98 percent and purity of 97 to 99 percent of diazinon which is only very slightly colored. This process is, thus, an improvement over the prior art in that a catalyst is not necessary; and it affords a product in excellent yield containing essentially no toxic thiotepp as by-product.

DETAILED DESCRIPTION OF THE INVENTION

The process of the present invention requires that the reaction of the hydroxypyrimidine with TPC be run in a solvent from which water can be removed azeotropically. Suitable solvents are aliphatic hydrocarbon solvents such as petroleum ether 60-40, petroleum ether 60-80, heptane, octane, hexane or cyclohexane, together with MEK, or instead MIBK can be used as the sole solvent. The ratio of MEK to other solvents may be 1:99 to 1:4. Most preferred as the solvent, however, is either MIBK alone or heptane or octane or a mixture thereof together with MEK.

The improved results of the present reaction are in large measure dependent on the use of potassium carbonate as base, added as a solid. The $K_2CO_3$ is preferably added in an excess, desirably no greater than 20% excess, and preferably 10–15% excess.

The reaction of the present invention may be run at a temperature of from 60° C. to 116° C. during the preparation of the potassium salt of the hydroxypyrimidine and at a temperature of from 50° C. to 120° C., preferably 80° C to 100° C. 110° C. during the subsequent reaction with TPC; and the time of reaction after adding TPC may be from 2 hours to 10 hours, preferably about four hours. Contrary to U.S. Pat. No. 5,034,529, excellent yields of high purity product are achieved even when the reaction is carried out on an industrial scale, e.g. in reactors having volumes of 100 liters or more, and even in reactors having volumes of more than 1000 liters.

The very high yield of the present invention may be further improved by recycling the unreacted hydroxypyrimidine, making this process even more commercially viable.

While the prior art discloses removing the water either prior to or simultaneously with reacting with TPC, several problems were found to result from such practice. Azeotropic distillation of the water prior to adding TPC using NaOH or KOH was found to require a long period of heating to remove the last traces of water from the solid chunks formed. The solid chunks made it almost impossible to properly stir the mixture after the addition of the TPC. U.S. Pat. No. 4,326,059 attempted to overcome this problem by azeotropically distilling off the water in the presence of a phase transfer catalyst. However, long reaction times were still required and the final product still contained thiotepp.

U.S. Pat. No. 4,066,642 attempted to overcome this problem by azeotropically distilling off the water simultaneously with the reaction with TPC. The results were long reaction times affording low yields of dark colored diazinon. Even the use of the solvents of the instant invention, but using sodium hydroxide or sodium carbonate, also caused sticking and prevented the formation of a workable suspension.

However, the process of the instant invention involving azeotropic distillation of hydroxypyrimidine in the presence of MIBK or an aliphatic hydrocarbon solvent, followed by adding dry solid potassium carbonate - and, when the first mentioned solvent is an aliphatic hydrocarbon, also MEK provides a product which uses only short reaction times and affords very high yields of almost colorless diazinon, having a very high purity, and without the need for the use of a catalyst.

While there is some superficial similarity between the method of U.S. Pat. No. 5,034,529 and the process of the present invention, the present process is more advantageous in the production plant when compared to the process of U.S. Pat. No. 5,034,529 because it utilizes a much shorter overall reaction time, e.g. the azeotropic distillation is completed in less than 2–3 hours and usually in less than 2 hours. A further advantage occurs due to the use of hydrocarbon/MEK as solvents, as the use of these solvents serves to reduce or avoid the formation of added related impurities which often form by the reaction at high temperatures between MIBK and a strong base such as sodium hydroxide and potassium hydroxide.

While the invention will now be described in connection with certain preferred embodiments in the following examples, it will be understood that it is not intended to limit the invention to these particular embodiments. On the contrary, it is intended to cover all alternatives, modifications and equivalents as may be included within the scope of the invention.

EXAMPLE 1

Laboratory Scale

A mixture of 170 g (1.05M) of 94% wet hydroxypyrimidine and 300 ml heptane were heated to reflux and the water azeotropically distilled off, over a period of one hour. The mixture was cooled to 70° C., 160 g dry potassium carbonate, and 10 ml MEK, and were added and heated to 95° C. for an hour. To this were added 190 g TPC over 30 minutes and the mixture kept at a temperature of 95° C. for three hours. The mixture was cooled to 70° C., water added, the pH adjusted to 12.5 to 13 with a sodium hydroxide solution, the water layer discharged and the operation repeated. Water was then added again, the pH adjusted to 1.5 to 2 by the use of sulfuric acid solution. After stirring the water was separated and a heptane solvent distilled off to afford 300 g diazinon at a purity of 98.7% in a yield of 97.4%. The diazinon was light straw in color.

EXAMPLE 2

Production Plant Scale

A mixture of 1,300 kg (8.04 kilomoles) hydroxypyrimidine and 3000 liters heptane were heated to reflux in an 8,000 liter stainless steel reactor and the water azeotropically distilled off over a period of three hours. The mixture was cooled to 70° C. and 1,260 kg of potassium carbonate, and 100 liters MEK, were added. The mixture was heated to 95° C. for an hour, 1,425 kg TPC were added over 30 minutes and the mixture was heated for three hours. The reactor was cooled to 70° C. and worked up as described above in Example 1. Distillation of the heptane afforded 2,250 kg of diazinon in a concentration of 98.7% and a yield of 97.4%, having a light straw color.

EXAMPLE 3 (Comparative)

Process of U.S. Pat. No. 5,034,529 In The Laboratory

A mixture of 170 g wet hydroxypyrimidin mole), 250 ml methyl isobutyl ketone (MIBK) and 80 g of a 50% sodium hydroxide solution was heated to 115° C. and the water was azeotropically distilled off, returning the MIBK to the flask. It took about 2.5 hours to distill off essentially all the water. The mixture was then cooled to 65° C. and 190 g (1 mole) of TPC was added over a period of 30 minutes. The reaction temperature was raised to 80° C. and held there for two hours. The mixture was worked up as described in U.S. Pat. No. 5,034,529 to give 300 g of diazinon at a purity of 98% and in a yield of 97%.

EXAMPLE 4 (Comparative)

Process of U.S. Pat. No. 5,034,529 In the Production Plant

A mixture of 1,300 kg (8.04 kilomoles) wet hydroxypyrimidine, 2,250 kg MIBK and 640 kg of 50% sodium hydroxide solution in an 8,000 liter stainless steel reactor was heated to 115° C. and the water azeotropically distilled off and separated from the MIBK. It took about 8 to 10 hours to remove 90% of the water and an additional 6 to 10 hours to remove a total of 99% of the water. The reaction mixture was cooled to 60° C. and 1,425 kg of TPC was added over 30 minutes. The reaction temperature was raised to 80° C. and held there for two hours. The mixture was worked up as before to give 2,234 kg of diazinon at a purity of 98.1% and in a yield of 98%. The color of the diazinon was yellow to brown.

This shows that the process of U.S. Pat. No. '529 does not work well in the production plant, because the distillation time is excessive.

EXAMPLE 5 (Comparative)

Preparation of Diazinon in the Presence of MIBK and 20% Na$_2$CO$_3$ Solution According to U.S. Pat. No. 5,034,529

A mixture of 352 g hydroxypyrimidine, 615 g MIBK and 1,360 g of 20% Na$_2$CO$_3$ solution in a 2-liter four-neck flask equipped with blade stirrers, dropping funnel, thermometer, oil bath, and azeotropic apparatus was heated to reflux and azeotropically dried, with the MIBK being returned to the flask. Water removal was completed in 6 hours. The mixture was cooled to 90° C. and 381 g of TPC is added over 30 minutes. The reaction was completed after 14 hours at 100° C. Washing was continued as described before and, after distillation in vacuum, 440 g of diazinon of 92% purity was obtained, a yield of 70%. This shows that the process of U.S. Pat. No. '529 using MIBK and Na$_2$CO$_3$ in the laboratory produces a poor yield.

EXAMPLE 6 (Comparative)

Preparation of Diazinon in the Presence of MIBK and Na$_2$CO$_3$

A mixture of 352 g hydroxypyrimidine (2.21 moles, 95.5% assay 3% water) and 615 g MIBK in a 1 liter four-necked flask equipped with blade stirrer, dropping funnel, thermometer oil bath and azeotropic apparatus was heated to reflux and azeotropically dried, with the MIBK being returned to the flask. Once water removal was complete, within half an hour the mixture was cooled to 90° C. and 275 g dry Na$_2$CO$_3$ were then added. Then 381 g (2 mole) of TPC were added over a period of 30 minutes. The reaction was complete after 14 hours at 100° C. Then 600 ml of water were added to dissolve the salts. After stirring the mixture for 15 minutes at 60° C., the phases were allowed to separate and the lower aqueous phase was discharged. Then 400 ml of water were added to the organic phase and the pH was adjusted to 13–13.5 with NaOH solution. After the mixture was stirred for 15 minutes at 60° C., the phases are allowed to separate. The lower aqueous phase was discharged and 400 ml of water was added. While the mixture was stirred, the pH was adjusted to 1.5–2.0 with hydrochloric acid. After 15 minutes the phases were allowed to separate and the lower layer was discharged; 400 ml of water were added and the pH was adjusted to 7.0–7.5 with 5% NaOH solution. After fifteen minutes the phases were allowed to separate and the lower aqueous layer was discharged. The wet MIBK solution was then vacuum distilled at up 100° and at 5 mm Hg pressure to afford 440 g of 97% assay diazinon at a yield of only 70%.

EXAMPLE 7 (Comparative)

Process of U.S. Pat. No. 5,034,529 Using Potassium Carbonate

A mixture of 170 g (1.05 moles) hydroxypyrimidine, 280 g MIBK and 160 g dry potassium carbonate were heated to 115° C. and the water azeotropically distilled off over a period of about five hours, during which a great deal of foaming occurred. The mixture was heated to 80° C. for one hour, cooled to 65° C. and 190 g (1 mole) of TPC was added over one hour. The mixture was heated to 80° C. and kept at this temperature for an additional two hours. The mixture was worked up as before, to afford 300 g of a light colored diazinon at a purity of 98.5% and a yield of about 98%.

This example shows that the process of U.S. Pat. No. '529, even when modified to use the K₂CO₃, is not satisfactory because of serious foaming and an excessive distillation time.

EXAMPLE 8

Process of the Present Invention in the Laboratory

A mixture of 170 g (1.05 moles) hydroxypyrimidine and 280 g MIBK were heated to 115° C. and the water azeotropically distilled off over a period of about two hours. The mixture was cooled to 80° C. and 160 g dry potassium carbonate was added. The mixture was heated to 80° C. for one hour, cooled to 65° C. and 190 g (1 mole) of TPC was added over one hour. The mixture was heated to 80° C. and kept at this temperature for an additional two hours. The mixture was worked up as before, to afford 300 g of a light colored diazinon at a purity of 98.5% and a high yield of about 98%.

EXAMPLE 9

Process of the Present Invention in the Production Plant

A mixture of 1,300 kg (8.04 kilomoles) hydroxypyrimidine and 2,250 kg MIBK were heated to 115° C. and the water azeotropically distilled off over a period of only two hours. The mixture was cooled to 65° C., 1,280 kg of dry potassium carbonate were added and the mixture heated at 80° C. for one hour. The mixture was cooled to 65° C., 1,470 kg of TPC were added over a period of 30 minutes, the mixture was heated to 80° C. and kept at this temperature for three hours. The mixture was worked up as before, to afford 2,312 kg of diazinon in a purity of 98.2% in a yield of 96.2%.

The foregoing description of the specific embodiments reveal the general nature of the invention so that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

EXAMPLE 10

Process of the present invention In The Production Plant

A mixture of 1,300 kg (8.04 kilomoles) of 94% wet hydroxypyrimidine and 2,250 kg heptane were heated to reflux and the water azeotropically distilled off, over a period of one hour. The mixture was cooled to 70° C. and 1,280 kg dry potassium carbonate was added and heated to 90° C. for an hour. To this were added 1,470 kg TPC over 30 minutes and the mixture kept at a temperature of 95° C. for three hours. The mixture was cooled to 70° C. water added, the pH adjusted to 12.5 to 13 with a sodium hydroxide solution, the water layer discharged and the operation repeated. Water was then added again. The pH adjusted to 1.5 to 2 by the use of sulfuric acid solution. After stirring, the water was separated and a heptane solvent distilled off to afford 2,312 kg diazinon at a purity of 98.7% in a yield of 97.4%. The diazinon was light straw in colour.

What is claimed is:

1. In a process for preparing diazinon comprising reacting wet or dry 2-isopropyl 4-methyl-6-hydroxypyrimidine with thiophosophorylchloride (TPC), the improvement comprising mixing said 2-isopropyl-4-methyl-6-hydroxypyrimidine with an organic solvent selected from the group consisting of methyl isobutyl ketone (MIBK) and an aliphatic hydrocarbon solvent, and removing water by azeotropic distillation;

then adding dry potassium carbonate to the reaction mixture to convert said 2-isopropyl-4-methyl-6-hydroxypyrimidine to its potassium salt in the absence of water; and adding less than a stoichometric amount of said TPC to form said diazinon.

2. A process according to claim 1, wherein, prior to said azeotropic distillation, at least one of said organic solvent and said hydroxypyrimidine is wet.

3. A method in accordance with claim 1, wherein said organic solvent is MIBK.

4. A process in accordance with claim 1, wherein said organic solvent is petroleum ether 60-140, hexane heptane, octane, cyclohexane or a mixture thereof.

5. A process according to claim 4, further comprising adding dry methyl ethyl ketone (MEK) following said azeotropic distillation and prior to adding said TPC.

6. A process in accordance with claim 5, wherein said MEK is added at a concentration of 1-20% based on total solvent content.

7. A process in accordance with claim 6, wherein said MEK is added at a percentage of approximately 5%.

8. A process in accordance with claim 1, wherein said potassium carbonate is present in excess.

9. A process according to claim 1, wherein the ratio of potassium carbonate to 2-isopropyl-4-methyl-6-hydroxypyrimidine is 1:1 to 1.2:1.

10. A process according to claim 1 wherein the ratio of potassium carbonate to 2-isopropyl-4-methyl-6-hydroxypyrimidine is 1.1:1 to 1.15:1.

11. A process in accordance with claim 1, wherein the temperature of reaction is 50° C. to 120° C.

12. A process in accordance with claim 1, wherein the temperature of reaction is 80° C. to 100° C.

13. A process in accordance with claim 1, wherein the time of reaction is 2-10 hours.

14. A process in accordance with claim 1, wherein the time of reaction is approximately 4 hours.

15. A process in accordance with claim 1, wherein said azeotropic distillation is completed in less than about 3 hours.

16. In a process for preparing diazinon comprising reacting wet or dry 2-isopropyl-4-methyl-6-hydroxypyrimidine with thiophosphoryl chloride (TPC) in a reactor, the improvement comprising mixing said 2-isopropyl-4-methyl-6-hydroxypyrimidine with methyl isobutyl ketone (MIBK), removing water by azeotropic distillation, then adding dry potassium carbonate to the reaction mixture to convert said 2-isopropyl-4-methyl-6-hydroxypyrimidine to its potassium salt in the absence of water, and adding less than a stoichiometric amount of said TPC to form said diazinon.

17. A process according to claim 16, wherein the MIBK and said 2-isopropyl-4-methyl-6-hydroxypyrimidine are wet.

18. A process according to claim 16, wherein the reactor has a volume of at least 100 liters.

19. A process according to claim 16, wherein the reactor has a volume of at least 1000 liters.

20. A process according to claim 16, wherein the weight ratio of potassium carbonate to 2-isopropyl-4-methyl-6-hydroxypyrimidine is 1:1 to 1.2:1.

21. A process according to claim 16, wherein the temperature of reaction is 50° C. to 120° C.

22. A process according to claim 16, wherein the temperature of reaction is 70° C. to 90° C.

23. A process according to claim 16, wherein the time of reaction is 2 to 10 hours.

24. A process according to claim 16, wherein the time of reaction is approximately 6 hours.

25. A process according to claim 16, wherein said azeotropic distillation is completed within 2 to 3 hours.

26. In a process for preparing diazinon comprising reacting wet or dry 2-isopropyl-4-methyl-6-hydroxypyrimidine with thiophosphoryl chloride (TPC), the improvement comprising mixing said 2-isopropyl-4-methyl-6-hydroxypyrimidine with an aliphatic hydrocarbon solvent, removing water by azeotropic distillation, optionally adding methyl ethyl ketone, adding dry potassium carbonate to the reaction mixture to convert said 2-isopropyl-4-methyl-6-hydroxypyrimidine to its potassium salt in the absence of water, and adding less than a stoichiometric amount of said TPC to form said diazinon.

27. A process according to claim 26, wherein, prior to said azeotropic distillation, at least one of said hydrocarbon solvent and said 2-isopropyl-4-methyl-6-hydroxypyrimidine contains water.

28. A process according to claim 26, wherein said hydrocarbon solvent is selected from the group consisting of petroleum ether having a boiling point of about 60°–140° C., heptane, octane, cyclohexane, hexane and mixtures thereof.

29. A process according to claim 26, further comprising adding dry methyl ethyl ketone following said azeotropic distillation and prior to adding said TPC.

30. A process according to claim 29, wherein said methyl ethyl ketone is added at a concentration of 1% to 20% by weight.

31. A process according to claim 30, wherein said methyl ethyl ketone is added at a concentration of 5%.

32. A process according to claim 26, wherein the temperature of reaction is 50° C. to 120° C.

33. A process according to claim 32, wherein the temperature of reaction is 80° C. to 110° C.

34. A process according to claim 26, wherein the time of reaction is 2 hours to 10 hours.

35. A process according to claim 34, wherein the time of reaction is approximately 4 hours.

36. A process according to claim 26, wherein said azeotropic distillation is completed in less than about 3 hours.

* * * * *